(12) United States Patent
Miller et al.

(10) Patent No.: US 7,037,691 B2
(45) Date of Patent: May 2, 2006

(54) KINASE MIMIC CATALYSTS FOR ASYMMETRIC SYNTHESIS OF PHOSPHORYLATED INOSITOLS AND CYCLOALKANOLS

(75) Inventors: Scott J. Miller, Natick, MA (US); Bianca Sculimbrene, Newton, MA (US); Adam J. Morgan, Scituate, RI (US)

(73) Assignee: The Trustees of Boston College, Chestnut Hill, MA (US)

( * ) Notice: Subject to any disclaimer, the term of this patent is extended or adjusted under 35 U.S.C. 154(b) by 464 days.

(21) Appl. No.: 10/187,208

(22) Filed: Jul. 1, 2002

(65) Prior Publication Data

US 2003/0100090 A1 May 29, 2003

Related U.S. Application Data

(60) Provisional application No. 60/302,621, filed on Jul. 2, 2001.

(51) Int. Cl.
*C12P 9/00* (2006.01)
*C07K 2/00* (2006.01)

(52) U.S. Cl. .................................. 435/131; 530/300
(58) Field of Classification Search ................ 435/131; 530/300
See application file for complete search history.

(56) References Cited

U.S. PATENT DOCUMENTS 3,280,098 A    10/1966 Otsuka et al. ............ 260/112.5
4,411,890 A *  10/1983 Momany .................... 514/17

OTHER PUBLICATIONS

Lahiri et al. "The Pentacovalent Phosphorus Intermediate of a Phosphoryl Transfer Reaction" Science (Mar. 23, 2003) 299: 2067–2071.*
Yarnell, A. "Caught in the Act. X–ray Study May have Trapped Transition State of Enzyme–Catalyzed Reaction" Chemical and Engineering News (Mar. 31, 2003) 81(13): 5.*
Copeland et al. "Minimal acylase–like peptides. Conformational control of absolute stereospecficity" J. Org. Chem. (1998) 63: 6784–6785.*
Lohmuller et al. "Toward computer–based cleavage sit prediction of cysteine endopeptidases" Biol. Chem. (2003) 384(6): 899–909.*
Haspel et al. "Reducing the computational complexity of Protein folding via fragment folding and assembly" protein Sci. (2003) 12:1177–1187.*
Nussinov Efficient computational algorithms for docking and for generating and matching a library of function epitopes II. Comb. Chem. High Throughput Screen (1999) 2(5): 261–69.*

Ludwig, J., et al. (1991). "Stereospecific Synthesis of Guanosine 5'–O(1,2–Dithiotriphosphates)," *J. Org. Chem.*, 56:5860–5865.

Sawada, T., et al. (1997). "Efficient Asymmetric Synthesis of Phosphatidyl–D–*myo*–inositol–3, 4, 5–triphosphate," *Chem. Pharm. Bull.*, 45(9):1521–1523.

Pietrusiewicz, K.M., et al. (1992). "The Synthesis of Homochiral Insitol Phosphates from *myo*–Insitol," *Tetrahedron*, 48(26):5523–5542.

Chenault, K.H., et al. (1998). "Kinetic Chiral Resolutions of 1,2–diols and Desymmetrization of Glycerol Catalyzed by Glycerol Kinase," *J. Org. Chem.*, 63:4039–4045.

Akiyama, T., (1996). "L–Quebrachitol as a New Chiral Building Block," *Journal of Synthetic Organic Chemistry Japan*, 54(2):84–93.

Papaioannou et al.(2001) "Enantioselective synthesis of a Mitosane Core Assisted by Diversity–Based Catalyst Discovery", Organic Letters, vol. 3, No. 18, pp. 2879–2882.

Sculimbrene et al. (2001) "Discovery of a Catalytic Asymmetric Phosphorylation Through Selection of a Minimal Kinase Minic: A Concise Total Synthesis of D–Myo–Inosito–1–Phosphate", CHEMTRACTS–Organic Chemistry, vol. 14, pp. 802–804.

Vasbinder et al. (2001) "Incorporation of Peptide Isosteres into Enantioselective Peptide–Based Catalysts as Mechanistic Probes", Angewandte Chemie, vol. 40, No. 15, pp 2824–2827.

International Search Report PCT/US02/20738.

* cited by examiner

*Primary Examiner*—Jean C. Witz
*Assistant Examiner*—Susan Hanley
(74) *Attorney, Agent, or Firm*—Palmer & Dodge, LLP; Paul Campbell Evans; David J. Dykeman

(57) ABSTRACT

The present invention provides peptide-based phosphorylation catalysts (PBPC's) for the asymmetric monophosphorylation of cyclitols, particularly myo-inositols. The PBPC's of the invention effect a regio and enantioselective phosphorylation of a myo-inositol in a manner analogous to enzymatic kinases, thereby functioning as effective "kinase mimics." Although orders of magnitude less complex in terms of structure than macromolecular proteins, the PBPC's of the invention control product formation with high enantioselectivity (>98% ee). The synthetic (+)-myo-inositol-1-phosphate is optically and spectroscopically equivalent to naturally occuring compound. The ability of the low molecular weight PBPC's of the present invention to mimic stereoselective enzymes represents a powerful approach toward catalytic asymmetric synthesis of biologically important molecules, and for mechanistic modeling of biochemical transformations to enable their use in drug applications.

17 Claims, 3 Drawing Sheets

KINASE MIMIC CATALYSTS FOR ASYMMETRIC SYNTHESIS OF PHOSPHORYLATED INOSITOLS AND CYCLOALKANOLS

This application claims priority to U.S. Provisional Application Ser. No. 60/302,621 filed on Jul. 2, 2001.

STATEMENT AS TO FEDERALLY FUNDED RESEARCH

The present invention was made with support in part from the National Institute of Health Grant No. GM-57595 and the National Science Foundation Grant No. CHE-9874963. The United States Government retains certain rights to the invention.

FIELD OF THE INVENTION

The present invention relates to catalyst materials that provide regioselective and enantio-selective phosphorylation of cyclitols, in particular inositols such as myo-inositol. Specifically, the present invention concerns phosphorylation catalysts and phosphorylation methods for regio- and enantioselective synthesis of D-myo-inositol-monophosphates.

BACKGROUND OF THE INVENTION

Cyclitols are cycloalkanes containing one hydroxyl group on each of three or more ring carbons. The most abundant members of the cyclitol genus are the inositols (1,2,3,4,5,6-hexahydroxy-cyclohexanes), the most important stereoisomer of this family being myo-inositol (I). Myo-inositol has hydroxyl groups in the 1-, 2-, 3-, and 5- positions of the cycloaliphatic ring that lie in one side of a stereochemical plane, and two hydroxyl groups in the 4- and 6-positions that lie on the other. Phosphorylated derivatives of cyclitols and inositols, wherein one or more hydroxyl groups are converted to phosphate monoesters, are generally referred to, respectively, as cyclitol phosphates or inositol phosphates.

The biological function of cyclitols, in particular inositols, depends on both the extent of phosphorylation of the hydroxyl groups, as well as the position and stereochemistry of the resulting phosphate functionalities. Complex proteins called kinases catalyze reactions that put phosphate groups on specific sites of a substrate. Cellular processes in mammals, including man, depend, at least in part, on inositol phosphates. Certain inositol phosphates function as "second messengers", that is, molecules that provide the means by which neurotransmitters, growth factors or hormones alter processes inside cells without necessarily penetrating the cells they affect. D-myo-inositol-1-phosphate is an important second messenger in cellular signal transduction pathways. Increased concentrations of these second messengers, in turn, activate certain enzymatic processes within the cells. Similarly, some growth factors such as platelet derived growth factor (PDGF) cause an increased production of inositol phosphates in the cells they affect. Intracellular concentrations of inositol phosphates also appear to play a role in the regulation of cell division and the inflammatory response. Because of the potential medicinal importance of the natural inositol phosphates, including its analogs, derivatives and isomers, there has been considerable interest in these compounds, which is reviewed in the art (*Science*, 234: 1519 (1986); *Scientific American*, 253: 142 (1985)).

Studies pertaining to medicinal application of inositol phosphates have, however, been limited both by low yields of isolable material from natural sources, and the tedious processes involved in their isolation and purification. This is mainly attributed to the fact that the inositol substrate offers not only multiple reactive sites, but also the possibility of enantiomeric products for each derivatized reactive site. Synthetic methods for preparing a desired enantiomer, therefore, usually involves either elaborate protecting-group strategies including use of chiral auxiliaries, or neccessitates laborious isolation, such as for example, by selective recrystallization or enzymatic resolution. Practical and efficient synthetic methods for selectively preparing significant larger amounts in high purity of specific enantiomers of phophorylated inositols and their analogs remain a largely unsolved issue. It is, therefore, desirable to develop efficient synthetic methods for providing adequate quantities of enantiomerically pure synthetic insitol phosphates for applications involving their medicinal use.

SUMMARY OF THE INVENTION

The present invention concerns the catalytic phophorylation of cycloalkanols, including cyclitols in a stereoselective manner to provide the corresponding cyclitol phosphates. Specifically, the present invention provides phosphorylation catalysts for the regio- and enantioselective phosphorylation of cyclitols, particularly myo-inositol to provide D-myo-inositol-mono-phosphates that are stereochemically equivalent to the corresponding naturally occuring compounds. The catalysts of the invention, in terms of their ability to effect stereoselective phosphorylations at specific hydroxyl groups in phosphorylate cyclitols, particularly myo-inositol, mimic the biologically occurring transformation by the action of complex kinases, and are hence termed to be "kinase mimics" in analogy to the histidine-dependent class of kinases that participates in cell-signaling pathways.

In one aspect, the present invention provides catalyst materials for the stereoselective phosphorylation of secondary alcohol functional groups in cyclitols, particularly myo-inositol in high enantiomeric excess (ee) in high yields relative to currently employed separation processes. The catalysts of the present invention comprise of a terminal heterocylic segment that includes an alkylimidazole moiety that is capable of functioning as a catalyst for alcohol phosphorylation in substoichiometric ratios in the presence of a phosphorylating agent. The phosphorylation catalysts of the invention additionally comprise a low molecular weight peptide-based segment that is chemically bonded to the terminal heterocyclic segment described above that renders the catalysts capable of imparting both high regio- and stereoselectivity in phosphorylation reactions involving cyclitols. They phosphorylation catalysts of the present invention are hereinafter defined as "peptide-based phosphorylation catalysts" (PBPC's).

In another aspect, the present invention provides synthetic methods for the efficient stereoselective (regio- and enantioselective) for phosphorylation of secondary alcohols groups in cyclitols particularly in the naturally occuring compound myo-inositol to yield corresponding phosphates in high enantiomeric excess (ee). Specifically, the phosphorylation catalysts of the present invention provides a stereoselective synthetic method for obtaining D-myo-inositol-monophosphates in high enantiomeric purity and in high yields relative to conventional processes that are identical to the corresponding naturally occurring products.

In yet another aspect, the present invention provides synthetic methods for creating a synthetic library comprising low-molecular weight polypeptide phosphorylation catalysts, and a "parallel reaction" method that enables the identification of individual members within the library that function as highly stereoselective catalyst materials for phosphorylation of cyclitol substrates, particulary myo-inositol. All individual members within the low-molecular weight polypeptide catalyst library of the invention comprise a terminal heteroalkyl segment that enable them to catalyze phosphorylation reactions of cyclitols such as myo-inositol, either for the same enantiomer or for the opposite enantiomer of the cyclitol substrate (e.g. myo-inositol) with respect to that of the original peptide segment in the catalyst. Individual catalysts within the library of the invention, therefore, mimic biological enzymes in their ability to effect both enantioselective mono-phosphorylation of cyclitols such as myo-inositol providing myo-inositol-monophosphate, and enantiodivergent phosphorylations, that is, effect divergent stereoselectivity in the resulting myo-inositol through formation of highly diverse three-dimensional intermediate structures. Prior to the present invention, the use of a peptide based phosphorylation catalysts to effect the stereoselective phosphorylation for the synthesis of enantioselective and enantiodivergent myo-inositol-monophosphates were not known.

DETAILED DESCRIPTION OF THE INVENTION

Figure 1:
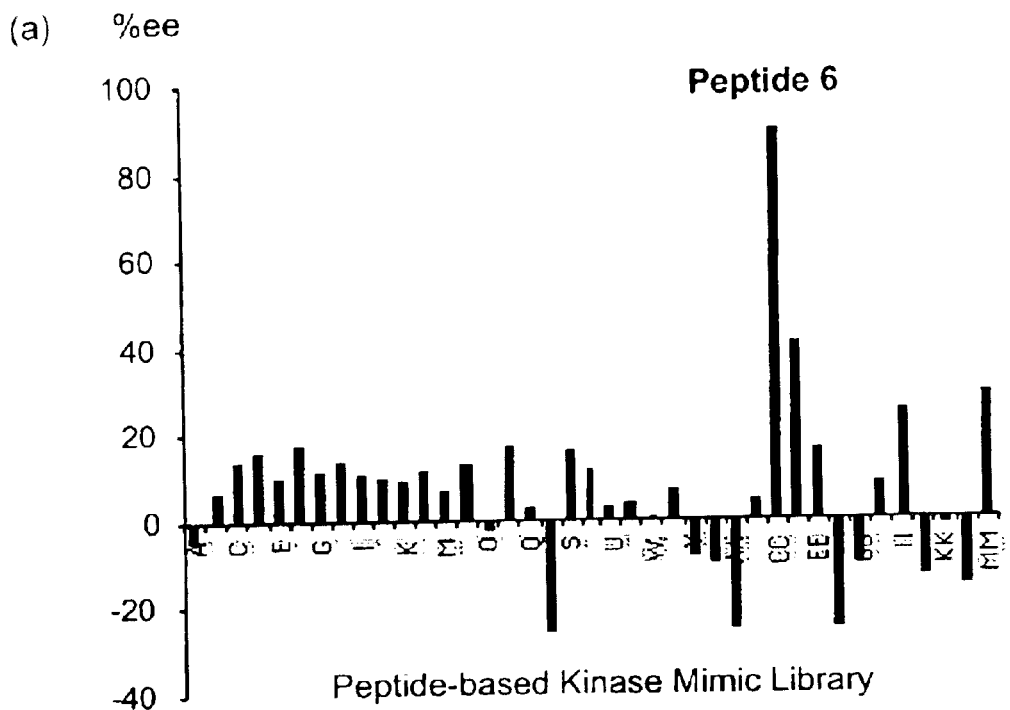
FIG. 1a shows the results of the library screening method for enantioselectivity of monophosphorylated of protected myo-inositol.
FIG. 1b shows the chemical structure of the most selective PBPC determined by the library screening and parallel reaction and assay method.
Figure 1:
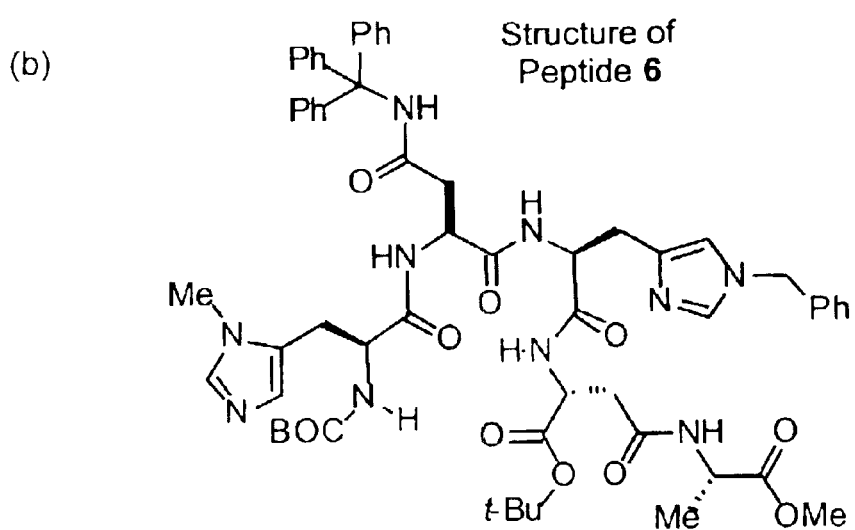

The following definitions describe the terms used throughout the specification and in the claims related to the present invention.

As used herein, the term "phosphorylation" means that the phosphorus in the phosphorylated compound is in the (+5) oxidation state, $P^{+5}$, as part of a phosphate monoester group.

As used herein "cyclitol monophosphates" or "inositol monophosphates" denote those phosphorylated derivatives of cyclitols or inositols that have one hydroxyl group converted to phosphate monoester.

As used herein stereoselective refers to the preferential formation in a chemical reaction of one stereoisomer over another.

As used herein enantioselective refers to the preferential formation in a chemical reaction of one enantiomer over another. Enantioselectivity and is quantitatively expressed by the enantiomeric excess (ee).

As used herein, regioselective refers to a chemical reaction wherein the product of reaction at one site in the substrate predominates over the product of reaction at other sites. This discrimination is also semi-quantitatively referred in terms of the magnitude of regioselectivity.

As used herein, enantiodivergent refers to preferential formation of an enantiomeric product from a reactant substrate that has an opposite optical rotation with respect to that of that of an asymmetric reactant or catalyst agent reacting with the reactant substrate.

The present invention provides phosphorylation catalysts for efficient asymmetric phosphorylation of cycloalkanols, in particular cyclitols such as myo-inositol, with high regio- and enantioselectivity. The present invention also provides methods utilizing these catalysts for synthesizing of myo-inositol-mono-phosphate, including D-myo-inositol-1-phosphate, which is an important second messenger in cellular signal transduction pathways. Although the chemical process of the present invention is directed primarily towards the synthesis of certain stereoisomers of myo-inositol-monophosphates, this process is applicable to the regio- and enantioselective synthesis of any cyclitol phosphate. The general principle of the chemical process of the present invention is illustrated in detail for myo-inositol-monophosphates.

The overall phosphorylation process of the present invention relies on high regio- and enantioselectivity provided by the phosphorylation catalysts of the invention, that when reacted in combination with a phosphorylation agent with a cyclitol such as myo-inositol, results in a highly stereoselective mono phosphorylation to give the corresponding myo-inositol-monophosphate in relatively high yield. The stereo selective control provided by the phosphorylation catalysts of the present invention includes both regioselecting (specific position in the cyclitol ring) and enatioselectivity preference for a specific enantiomer the phosphorylation process of the hydroxyl substituents of cyclitols. Scheme 1, which shows the conversion of myo-inositol to D-myo-inositol-1-phosphate (D-I-1P, equation 1) by the PBPC of the invention.

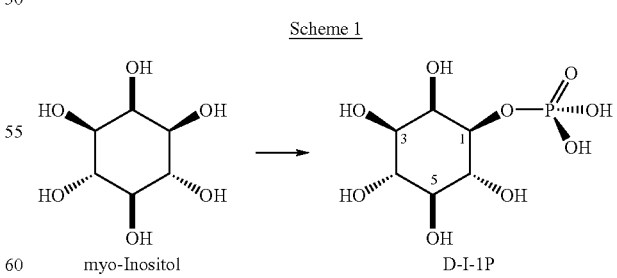

Scheme 1 myo-Inositol           D-I-1P

It should be noted that in conventional nomenclature, the three adjacent syn hydroxyl groups of myo-inositol are always designated as occupying the 1, 2, and 3 positions. Since myo-inositol possesses a plane of symmetry (i.e., it is a meso isomer), the 1 and 3 positions and the 4 and 6 positions are identical. When one of these positions is modified, two enantiomers are possible, and the nomenclature for these compounds can become ambiguous. For example, the name 1(R)-myo-inositol phosphate represents the same molecule as 3(S)-myo-inositol phosphate. Thus, for clarity, all products and synthetic intermediates are referred to herein by their net optical rotation, namely dextrorotatory (D) ((+) enatiomer use a positive net optical rotation) or levorotatory (L), ((−) enomtiomer wire a negative net optical rotation) using the numbering system of the desired final product.

One or more hydroxyl groups on the cyclitol substrate may, as is usually desired, be "protected" by one or more "protecting groups", and the term "protected hydroxyl group" indicates this type of protected derivatives. During phosphorylation reactions of the type described herein, protected hydroxyl groups do not react with the phosphorylating agent under reaction conditions of the phosphorylation process. The concept of using protecting groups to mask reactive functional groups is well understood in the field of synthetic chemistry and is discussed extensively, for example, in Green, *Protective Groups in Organic Synthesis*, John Wiley & Sons, N.Y. (1981).

The concept that one skilled in the art can prepare a cyclitol starting material such as for example, an inositol, with the appropriate number (0 to 5) and types of protecting groups located on preselected hydroxyl groups is denoted by the terminology "optionally protected". Suitable protecting groups for the hydroxyl groups of the cyclitol compounds include, but are not limited to, ethers, silyl ethers, esters, orthoesters, carbonates, cyclic acetals, cyclic ketals, cyclic orthoesters, and cyclic carbonates. Preferred protecting groups include benzyl ethers, benzoate esters and cyclohexylidene ketals. In a preferred embodiment, the optionally protected cyclitol is myo-inositol, wherein the hydroxyl groups in the 2, 4 and 6- positions are protected with benzyl ether (Bn) by the reaction of myo-inositol with benzyl bromide (BnBr) to the corresponding benzyl ether compound 3 as shown by in Scheme 2.

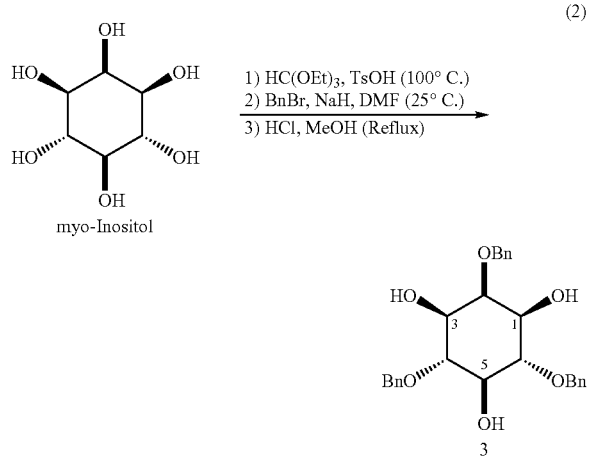

The asymmetric phosphorylation of process of myo-inositol illustrated in Scheme 1 involves a key step that utilizes the PBPC's of the invention that function as kinase mimics in effecting a regio- and enantio-selective phosphorylation of the protected myo-inositol 3 yield phosphorylated compound (−) 4 in a substantially optically pure form. A subsequent one-step deprotection of the protected hydroxyl groups affords the corresponding D-myo-inositol-monophosphate, namely D-myo-inositol-1-phosphate (D-I-1P). The reaction sequence and intermediate products involved in this process are illustrated Scheme 3.

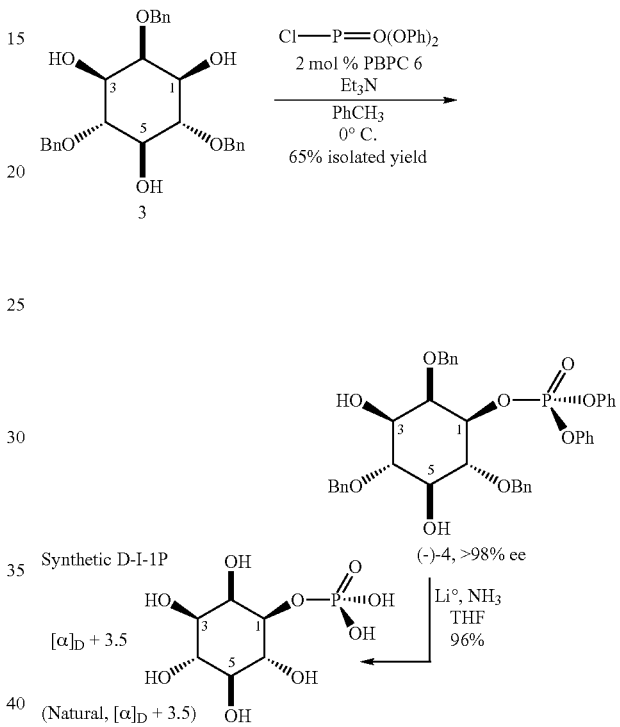

The synthetically obtained D-I-1P by the process illustrated in Scheme 3 using the (PBPC's) of the present invention is both optically and structurally (spectroscopically) equivalent to that of the same compound isolated from natural sources. Thus, although orders of magnitude less complex in terms of structure than a macromolecular protein (kinase), the peptide segment of the PBPC's of the invention provide a substantial control over the product sterochemistry, with almost total enantioselectivity (>98% ee). Due to their ability to mimic stereoselective biological enzymes, low molecular weight phosphorylation catalysts of the invention, represent a potentially powerful approach to catalytic asymmetric synthesis of biologically occurring compounds and for mechanistic modeling of biochemical transformations for their utilization in medicinal applications.

The peptide based catalysts of the present invention are described by the general formula I and comprising a heterocyclic terminal group, namely an imidazole group and an peptide segment "Pep".

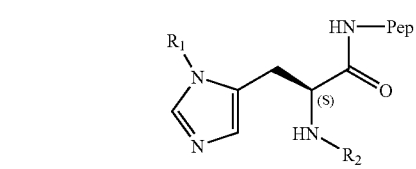

$R_1$ = lower alkyl
$R_2$ = amine protecting group
Pep = peptide segment

In one embodiment $R_1$ is lower alkyl, $R_2$ amine protecting group, preferably a carbamate group. Preferred carbamates include, but are not limited to, t-butyl carbamate (BOC), 9-fuorenylmethyl carbamate (FMOC, benzyl carbamate (CBz) and ortho-nitrobenzyl carbamate. Pep is a peptide segment P comprising a synthetic peptide residue, including but not limited to, an oligopeptide or a polypeptide residue. In a preferred embodiment, the peptide residue is a polypeptide comprising from about 2 to about 50 amino acids, and preferably, between about 2 to about 10 amino acids. In a preferred embodiment, $R_1$ is methyl ($CH_3$ or Me) and $R_2$ is t-butyl carbamate (BOC).

The low molecular-weight PBPC's of the invention function in a manner analogous to first step of a biological process comprising a series of signal transduction cascades involving myo-inositol. This step involves phosphorylation of histidine, which is effected by kinase action via a nucleophilic catalytic mechanism. The proposed catalytic phosphorylation process for cyclitols using the catalysts of the present invention is shown in Scheme 4. An inositol substrate, namely protected myo-inositol 3 is catalyzed by PBPC 1 in the presence of a phosphorylation agent, such as for example, diphenylchloro-phosphate (DPCP). The PBPC's of the present invention which are essentially based on modified histidine (His) residues (e.g., 1) presumably function in a manner analogous to His-dependent kinases to form a phosphorylated catalyst intermediate represented by 2. Based on the pendant peptide sequence, a functionalized, high energy phospho-imidazolium ion is generated in a chiral environment, that potentially interacts with multifunctional cyclitol substrates, including myo-inositol in a site-specific manner. As a result, phosphate transfer to substrate, such as for example, protected myo-inositol 3 can occur with both regio- and enantioselectivity to provide the corresponding enantio- and regiopure phosphate 4, regenerating catalyst 1 and rendering it available for another catalytic cycle.

Scheme 4

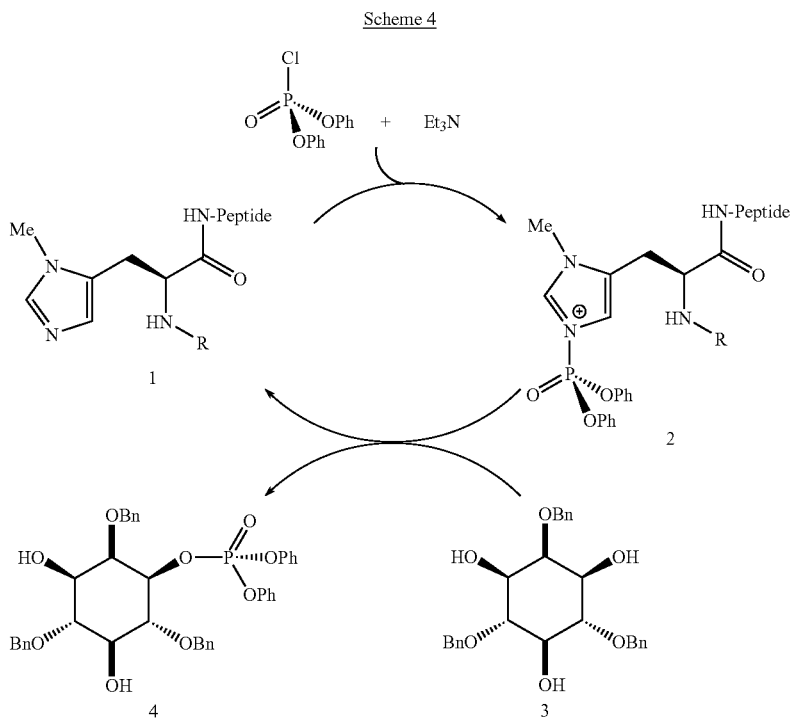

The terminal alkylimidazole segment in the PBPC's of the invention (such as that present in 1), functions efficiently as a catalyst for phosphorylation of alcohols in substoichiometric ratios. The proposed was made of action for the PCPC's of the present invention substantiated by model reactions involving phosphorylation of cycloaliphatic secondary alcohols by DPCP, which occurs with a high degree of enantioselectivity in the presence of a catalytic amount (2 mol % relative to DPCP) of N-methylimidazole (NMI) is present in the terminal histidine segment in the PBPC's. Table 1 summarizes the data from the model catalytic phosphorylation reactions. As is evident from the model reactions, relatively high degrees of conversions of (about 66 to about 95%) is achieved during the catalytic phosphorylation of several cyclic secondary alcohols (Table 1). Under identical conditions, the uncatalyzed rate of conversion (phosphotriester formation in the absence of NMI) is negligible (<5%). Efficient catalytic turnover in the phosphorylation process of the invention is achieved by inclusion of a stoichiometric amount of Et$_3$N as an additive during the reaction.

TABLE 1

Amine-based Catalysis of Alcohol Phosphorylation.[a]

[Reaction scheme: R$_2$CH-OH + Cl-P=O(OPh)$_2$, 2.5 mol % NMI, Et$_3$N, CH$_2$Cl$_2$ → R$_2$CH-O-P(=O)(OPh)(OPh)]

Cyclopentyl phosphate: 95%
Cycloheptyl phosphate: 86%
Cyclooctyl phosphate: 66%

[a]Analysis by $^1$H NMR (400 MHz). Reactions were quenched after 12 h.

The low molecular weight PBPC's of the present invention afford substantially high enantioselectivities in phosphorylation of cyclitols such as myo-inositol in nonpolar solvents. Myo-inositol is therefore, protected as the benzylether derivative 3 (Scheme 2), where the benzylther functionalities (i) confer solubility in non-polar solvents, and (ii) increase the regioselectivity of the phosphorylation process by reducing the site-selectivity problem to three unique unprotected hydroxyl groups.

Figure 2:
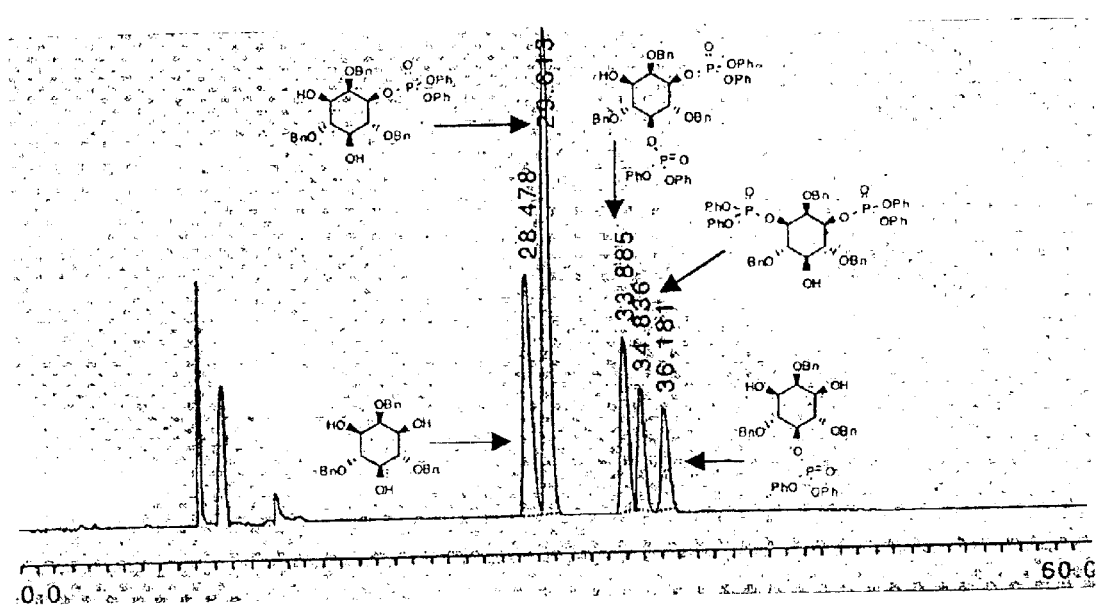
FIG. 2 shows product identification by the parallel reaction method of the invention by achiral/chiral HPLC assay.

The relative stereoselective efficiency of the PBPC's of the present invention is determined by a library screening method coupled with a parallel reaction array screening a chemically synthesized library of PBPC's of the general formula I, wherein the peptide group is a polypeptide, and is varied as a function of both the number and sequence of amino acids in the polypeptide chain. The library screening method of the invention involves a chemically synthesized library comprising one or more individual library members that are synthesized on a solid support by standard methods known in the art using commercially available polystrene resin preloaded with the appropriate amino acid. In one embodiment, a peptide library of about 39 members is generated and subsequently screened for regio- and enantioselectivity for monophosphorylation of protected myo-inositol derivative 3. The library is then examined in conjunction with the parallel reaction assay, wherein 39 independent phosphorylation reactions (one for each library member) of protected myo-inositol derivative 3 by individual library members is carried out under substantially identical conditions (0° C., 2 mol % unpurified PBPC in toluene (PhCH$_3$) solvent). FIG. 1 shows one example of the parallel screening method of the present invention wherein the enantio-selectivity for phosphorylation of the 1- versus 3-hydroxyl positions of the protected myo-inositol derivative 3 is used to identify the polypeptide segment in the PBPC that provides the highest regio- and enantioselectivity in the phosphorylated product (FIG. 1a). A two-stage achiral/chiral HPLC assay is then performed on the reaction mixtures to determine the overall product distribution. FIG. 2 shows the product identification assay by the achiral/chiral HPLC assay method. In the example shown, PBPC 6 comprising a pentapeptide shows the highest enantioselectivity (FIG. 1b). It is evident from the screening data (FIG. 1a) that each PBPC catalyst in the library affords a different level of enantioselectivity for the catalytic phosphorylation, underscoring the influence of peptide secondary structure in the PBPC's on the stereochemical outcome in the phosphorylated myo-inositol product. Pentapeptide 6, in its unpurified form provides the phosphorylated myo-inositol derivative (−)-4 (Scheme 4) with good enantioselectivity (90% ee) under the parallel screen conditions.

The PBPC catalyst comprising a peptide segment identified to provide the highest regio- and enantioselectivity by the screening method of the invention described herein, such as for example PBPC6, is then re-synthesized, purified to chromatographic homogeneity and utilized in a PBPC catalyzed asymmetric total synthesis of myo-inositol-monophosphate. In one embodiment, the PBPC catalyst 6 comprising the pentapeptide segment peptide is used in the synthesis of (D)-I-1P as illustrated in Scheme 2. Treatment of myo-inositol derivative 3 with DPCP and Et$_3$N (1 equiv), 2 mol % purified 6 in PhCH$_3$ (0° C.) provides the corresponding monophosphate (−)-4 as a single enantiomer (>98% ee by chiral HPLC, with about 70% conversion and about 58% isolated yield). Optically pure (−)-4 then converted to D-I-1P (which may be also represented as (+)-I-1P) in a single step by deprotection of the protected hydroxyl groups in about 73% isolated yield. The optical rotation of enantiomerically pure D-I-1P compound synthesized by the catalytic process of the present invention is identical to the naturally occurring compound (synthetic: [α]$_D$+3.5 c 1.0, pH=9: natural: [α]$_D$+3.5 c 1.0, pH=9). The catalytic process of the invention is relatively more efficient for obtaining D-I-1P than its isolation from natural sources, providing >150 mg of synthetic D-I-1P from about 500 mg of myo-inositol in a laboratory scale process. It is therefore, readily amenable to scale-up in a commercial process, both due to its simplicity in terms of the number of individual steps involved, and the high enantiomeric purity and relativel yields of the product.

The PBPC catalysts of the invention can also be optimized to effect an enantiodivergent phosphorylation of cyclitols, in particular, myo-inositol. They are, therefore, capable of functioning in similar manner to enzymes that perform enantiodivergent chemical transformations in biologic systems. This characteristic is particularly noteworthy in the case of enzymes that perform enantiodivergent chemistry is a biological environment, since they are composed almost exclusively of L-amino acids; completely enantiomeric enzymes composed entirely of D-amino acids, are relatively found in nature. In one embodiment, the PBPC catalyst of the present invention comprising a pentapeptide segment can be used in a catalytic phosphorylation reaction of a cyclitol, such as for example myo-inositol that is highly enantioselective for the opposite enantiomer of the inositol substrate with respect to the original peptide segment in the PBPC. A preferred embodiment of an enantiodivergent phosphorylation of myo-inositol with the PBPC catalyst of the present invention is shown in Scheme 5. The protected derivative of myo-inositol 2 is reacted with a phosphorylating agent (DPCP) in the presence of PBPC 24 to yield the corresponding monophosphate derivative 4(3-P), which is subsequently subjected to a deprotection reaction to yield the enantiodivergent monophosphate D-1-3P (Scheme 5).

Scheme 5

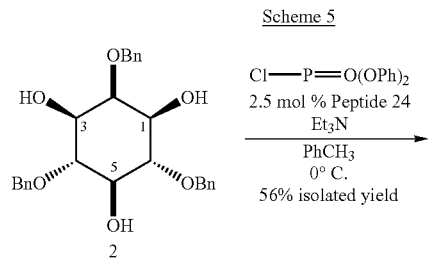

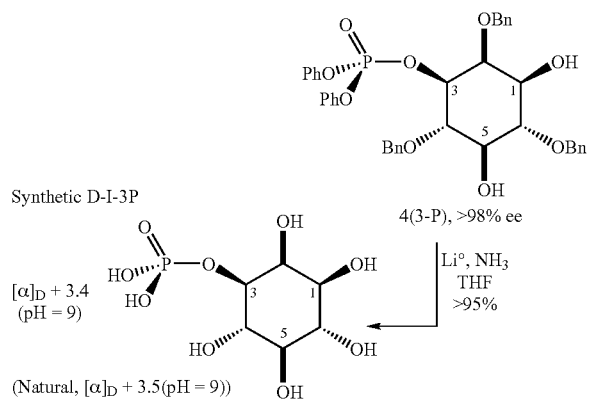

Figure 3:
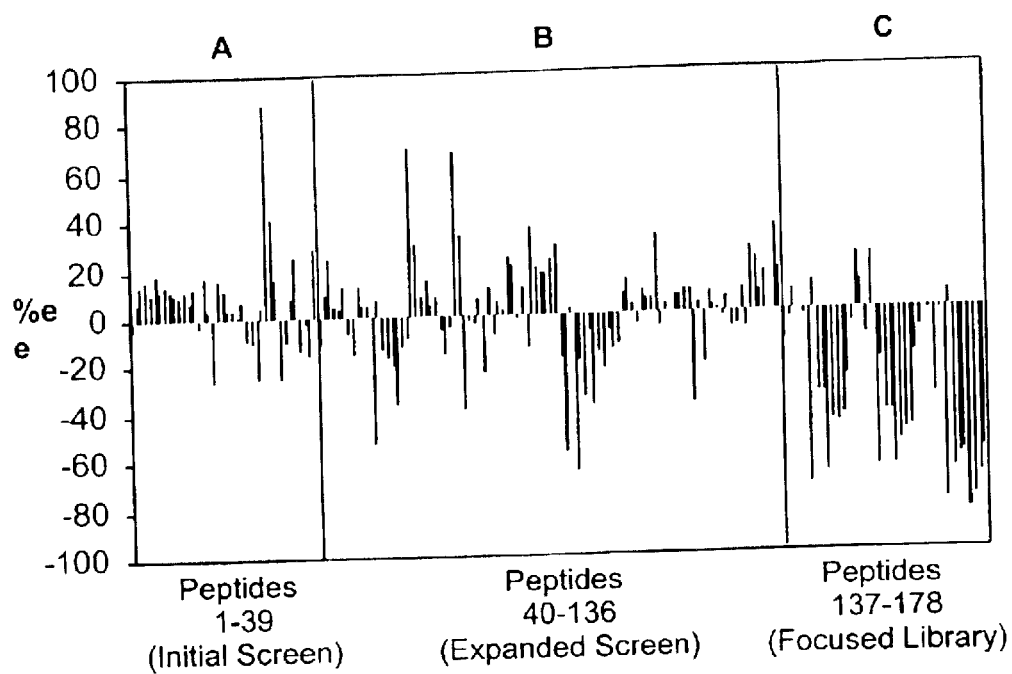
FIG. 3 shows the screening data for enantioselective phoshorylation of protected myo-inositol catalyzed by PBPC's.
Figure 3:
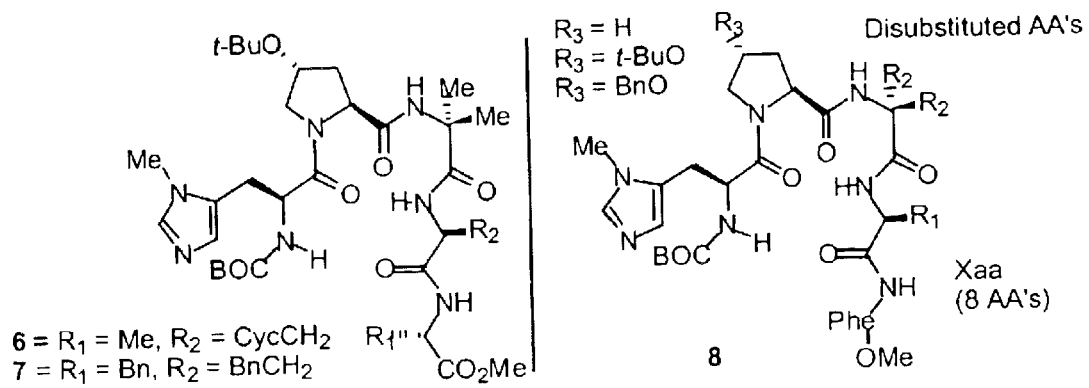

The PBPC's providing the highest regio- and enantiodivergent cyclitol monophosphate products, particularly myo-inositol-monophosphate is determined by the library screening method and "parallel reaction" method of the present invention described herein, whereby highly enantioselective PBPC's are by screening of a combination of random and focused libraries. FIG. 3 shows one example of the random and focused library screening method of the invention. The initial screen (FIG. 3A) of small peptide catalysts for asymmetric phosphorylation of protected myo-inositol substrate 2 (Scheme 5) is based on 39 peptides (tetra-through octapeptides) that contain a L-π(Me)-histidine nucleophilic residue. A number of PBPC's that selectively phosphorylate the 1-position of substrate 2 to give 4(1-P) are isolated within this library, as well as others that are selective for the enantiotopic 3-position, albeit with relatively lower selectivity. The choice of individual library members forming the initial 39-member is primarily based on synthetic sequences that are soluble in organic solvents. The results of the expanded screen are shown in FIG. 3B, wherein unpurified peptides were screened at room temperature.

PBPC's from both the initial and expanded screens (peptides 1–136) are selected on the both on the basis of sequences that are biased to form β-turns and β-hairpins in organic solvents, and on breadth of diversity in the amino acid sequences. To achieve diverse sequences, a randomization algorithm is utilized to afford sequences that are, in principle, unrelated. In one preferred embodiment, PBPC 5 comprising a pentapeptide is chosen as the core structure, following which a letter for each of 16 amino acid monomers is then assigned. The algorithm subsequently delivered 80 random sets of three-letter combinations. These are inserted into the core structure 5, following which individual members are synthesized for the library screening and parallel assay method of the invention.

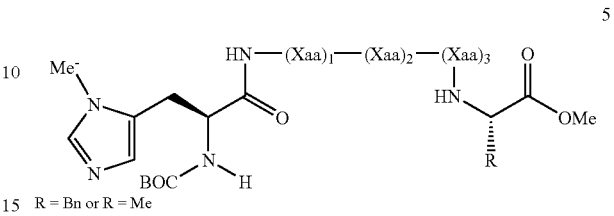

R = Bn or R = Me

The results of the expanded screen were striking in that the distribution of catalysts that were selective for the enantiotopic 1- and 3-positions are almost statistical. For example, in the expanded screen two new sequences 6 and 7 (FIG. 3) provide the enantiodivergent product 4(3-P) in >55% ee; similarly, two other sequences are selective for the enantiotopic 4(1-P) in >55% ee. Since the extent of enantioselectivity for the formation of the phosphorylated product in these desymmetrization reactions is related to the overall conversion of the reaction be this issue, overinterpretation of small differences in the ee of the isolated 4(3-P) is avoided. Although the conditions utilized in the library screening method of the present invention is designed to produce the protected myo-inositol-monophosphate at about 70% conversion for the highly enantioselective members, less selective members of the library also distribute themselves into enantiodivergent groups (83 selective for 4(1-P), 51 selective for 4(3-P)) (FIGS. 3A and 3B). In a preferred embodiment, PBPC's 6 and 7 (FIG. 3) are chosen for the selective catalytic phosphorylation process for obtaining 4(3-P), since they are both moderately selective for 4(3-P). PBPC's 6 and 7 are in the β-turn family, in comparison to PBPC 1, which has its origin in the random library. A focused library 8 is then designed around these selected individual members.

In one embodiment, the L-Hyp residue ($R_3$ in FIG. 3) is exchanged with L-Pro and BnHyp in a 42-member library. Further, the geminal substitution in the i+2 position is varied α-amino-α-methylalanine (Aib) and spirocyclic groups. Additionally, least eight other residues are appended in the i+3 position we explored 8 other residues to achieve a 42-member library. The library screening data for the individual members is shown in FIG. 3C and in Table 2.

From individual library members (PBPC's) that are selective for the enantiotopic 4(3-P) (Scheme 5), the following trends are summarized (Table 2): (1) A 5-membered spirocyclic residue in the i+2 position contributes to catalyst selectivity (PBPC's 10, 15 and 20) (2) a t-BuTyr at the i+3 position provides increased selectivity (PBPC's 13, 18 and 23).

TABLE 2

Selected Data from Focused[a]

| Cataly | i + 1 | i + 2 | i + 3 | 4(3-P)ee |
|--------|-------|-------|-------|----------|
| 7 | t- | Aib | Hfe | 65 |
| 10 | t- | spiro- | Hfe | 84 |
| 11 | t- | spiro- | Hfe | 78 |
| 12 | t- | spiro- | Hfe | 36 |
| 13 | t- | Aib | t-BuTy | 79 |
| 14 | BnHy | Aib | Hfe | 55 |
| 15 | BnHy | spiro- | Hfe | 66 |
| 16 | BnHy | spiro- | Hfe | 42 |
| 17 | BnHy | spiro- | Hfe | 10 |
| 18 | BnHy | Aib | t-BuTy | 66 |
| 19 | Pro | Aib | Hfe | 47 |
| 20 | Pro | spiro- | Hfe | 68 |
| 21 | Pro | spiro- | Hfe | 35 |
| 22 | Pro | spiro- | Hfe | 0 |
| 23 | Pro | Aib | t-BuTy | 72 |

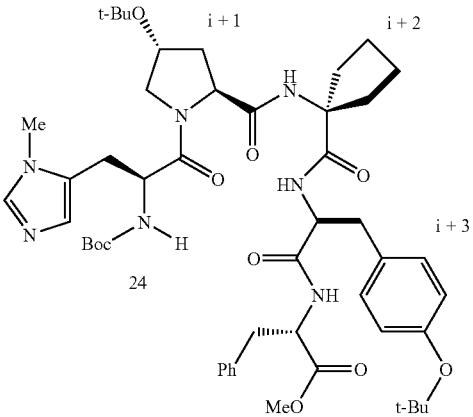

[a]Screen was performed with unpurified catalysts (2.5 mol %, 25° C.), uniformly quenched after 6 h. See Supporting Information The trends obtained from the library screening assay of the present invention can be used to optimize the functional groups at the i+3 position. In the embodiment whose library screening results are shown in Table 2, it can be concluded that PBPC's comprising a 5-membered ring in combination with t-BuTyr at the i+3 position is likely to yield a superior catalyst in terms of selectivity. Based on such analysis, a non-library member PBPC 24 (Table 2) prepared by independent synthesis exhibits high selectivity for the formation of 4(3-P), affording the product in about 94% ee at about 70% conversion even under the un-optimized conditions of the screen. The optimized PBPC 24 can be used for the total synthesis of D-myo-inositol-3-phosphate (D-I-3P) as shown in Scheme 6, in a manner analogous to the synthesis of enantiomeric D-I-1P (Scheme 3). In one example, desymmetrization of substrate 2 provides 4(3-P) with almost complete enantiopurity (>98% ee, about 56% isolated yield) using PBPC 24 under optimized conditions (2.5 mol %, 0° C., 4 h). The phosphorylated intermediate 4(3-P) is subsequently deprotected in a single step to give synthetic D-I-3P, whose characteristics match literature values.

The library screening assay of the present invention, by using a combination of random and focused libraries, enables the identification of low molecular-weight PBPC's (small molecule peptides) that are capable of selecting for specific positions for phosphorlyation of cyclitols. Specifically, such PBPC's are capable of selecting for either the 1-position or the enantiotopic 3-position during catalytic phosphorylation of an inositol derivative.

The library screening assay of the present invention can be used for the identification of catalysts that allow for enantio- and regioselective functionalization of other polyfunctionalized molecules, including biologically important ones, that may be of importance in medicinal applications.

EXAMPLES

General Procedures. Proton NMR spectra were recorded on Varian 400 or 300 spectrometers. Proton chemical shifts are reported in ppm ($\delta$) relative to internal tetramethylsilane (TMS, $\delta$ 0.0) or with the solvent reference relative to TMS employed as the internal standard (CDCl$_3$, $\delta$ 7.26 ppm; d$_6$-DMSO, $\delta$ 2.50; C$_6$D$_6$, $\delta$ 7.16 ppm; D$_2$O, $\delta$4.79). Data are reported as follows: chemical shift (multiplicity. [singlet (s), doublet (d), triplet (t), quartet (q), and multiplet (m)], coupling constants [Hz], integration). Carbon NMR spectra were recorded on Varian 400 (100 MHz) or 300 (75 MHz) spectrometers with complete proton decoupling. Carbon chemical shifts are reported in ppm ($\delta$) relative to TMS with the respective solvent resonance as the internal standard (CDCl$_3$, $\delta$ 77.0). Phosphorous NMR spectra were recorded on Varian 400 (162 MHz) spectrometer with complete proton decoupling. Phosphorous chemical shifts are reported in ppm ($\delta$) relative to a 85% H$_3$PO$_4$ external standard. NMR data were collected at 25° C., unless otherwise indicated. Infrared spectra were obtained on a Perkin-Elmer Spectrum 1000 spectrometer. Analytical thin-layer chromatography (TLC) was performed using Silica Gel 60 F254 precoated plates (0.25 mm thickness). TLC R$_f$ values are reported. Visualization was accomplished by irradiation with a UV lamp and/or staining with KMnO$_4$ or cerium ammonium molybdenate (CAM) solutions. Flash column chromatography was performed using Silica Gel 60A (32–63 µm). Optical rotations were recorded on a Rudolf Research Analytical Autopol IV Automatic polarimeter at the sodium D line (path length 50 mm). Elemental analyses were performed by Robertson Microlit (Madison, N.J.). High resolution mass spectra were obtained at the Mass Spectrometry Facilities either of the University of Illinois (Urbana-Champaign, Ill.), or Boston College (Chestnut Hill, Mass.). The method of ionization is given in parentheses.

Analytical and preparative reverse phase and normal phase HPLC were performed on a Rainin SD-200 chromatograph equipped with a single wavelength UV detector (214 nm or 254 nm). Analytical normal phase HPLC was performed on a Hewlett-Packard 1100 Series chromatograph equipped with a diode array detector (214 nm and 254 nm).

All reactions were carried out under an argon or nitrogen atmosphere employing oven- and flame-dried glassware. All solvents were distilled from appropriate drying agents prior to use. Diphenyl chlorophosphate was distilled prior to use and stored in a Schienk tube for no more than 2 weeks 2,4,6-Tri-O-berizyl-myo-inositol (3) was prepared according to a prior art method (Billington et al., *J. Chem. Soc. Perkin Trans. I*, (1989), 1423).

Example 1
Phosphorylation of Secondary Alcohols (Model Reactions)

The phosphorylation of alcohols in Table 1 was carried out in the following manner: Cyclopentanol (0.060 mL, 0.66 mmol) was dissolved in 25 mL of toluene and an aliquot of N-methyl imidazole in $CH_2Cl_2$ (50 µL, 0.017 mmol, 2.5 mol %) was delivered. Triethylamine (0.185 mL, 1.33 mmol) was added followed by diphenyl chlorophosphate (0.275 mL, 1.33 mmol). After 12 h the reaction was quenched with 2 mL of methanol and concentrated under reduced pressure. The compound was purified by silica gel flash chromatography, eluting with a gradient of hexanes to 15% ethyl acetate/hexanes, to yield 0.158 g (75% yield) of alcohol Diphenyl cyclopentane phosphate as a viscous liquid.

Diphenyl Cyclopentane Phosphate
$^1$H NMR ($CDCl_3$, 400 MHz) δ 7.35–7.31 (m, 5H), 7.23–7.16 (m, 5H), 5.14 (m, 1H), 1.94–1.69 (m, 6H), 1.65–1.54 (m, 2H);
$^{13}$C NMR ($CDCl_3$ 100 MHz) δ 150.4 (d, J=7.6 Hz), 129.5, 124.9, 119.9 (d, J=4.6 Hz), 83.3 d, J=6.9 Hz), 33.9 (d, J=5.3 Hz), 22.9;
$^{31}$P NMR ($CDCl_3$, 162 MHz) δ–13.8;
IR (film, cm$^{-1}$) 3490, 3062, 2968, 1596, 1486, 1287;
TLC R$_f$ 0.23 (20% ethyl acetate/hexanes);
Anal. Calcd. for $C_{17}H_{19}O_4P$: C, 64.15; H, 6.02; P, 9.73. Found: C, 64.23; H, 6.02; P, 9.79;
Exact mass calcd for $[C_{17}H_{19}O_4P+Na]$+requires m/z 341.0919. Found 341.0919 (ESI+).

Diphenyl Cycloheptane Phosphate
$^1$H NMR ($CDCl_3$, 400 MHz) δ 7.36–7.3.1 (m, 4H), 7.23–7.15 (m, 6H), 4.80 (m, 1H), 1.99 (m, 2H), 1.82 (m, 2H), 1.68–1.50 (m, 6H), 1.39 (m, 2H);
$^{13}$C NMR ($CDCl_3$, 100 MHz) δ 150.6, 129.5, 125.0, 120.0 (d, J=5.3 Hz), 82.2 (d, J=6.9 Hz), 35.4 (d, J=4.6 Hz), 28.0,22.1;
$^{31}$P NMR ($CDCl_3$, 162 MHz) δ–12.0;
IR (film, cm$^{-1}$) 3496, 3069, 2936, 1941, 1590, 1487, 1288;
TLC R$_f$ 0.38 (20% ethyl acetate/hexanes);
Anal. Calcd. for $C_{19}H_{23}O_4P$: C, 65.89; H, 6.69; P, 8.94. Found: C, 65.9.6; H, 6.49; P, 8.85;
Exact mass calcd for $[C_{19}H_{23}O_4P+Na]$+requires m/z 369.1232. Found 369.1217 (ESI+).

Diphenylcyclooctane Phosphate
$^1$H NMR ($CDCl_3$, 400 MHz) δ 7.35–7.10 (m, 10H), 4.79 (m, 1H), 1.97–1.85 (m, 4), 1.72–1.43 (m, 10H);
$^{13}$C NMR ($CDCl_3$, 100 MHz) δ 150.5 (d, J=6.9 Hz), 129.5, 125.0, 120.0 (d, J=4.6 Hz), 82.3 (d, J=6.9 Hz), 32.4 (d, J=3.8 Hz), 27.3, 24.9, 22.2;
$^{31}$P NMR ($CDCl_3$, 162 MHz) δ–11.9;
IR (film, cm$^{-1}$) 3478, 3068, 2917, 1948, 1589, 1489, 1284;
TLC Rf 0.41(20% ethyl acetate/hexanes);
Anal. Calcd. for $C_{20}H_{25}O_4P$: C, 66.66; H, 6.99; P, 8.59. Found: C, 66.53; H, 6.82; P. 8.30;
Exact mass calcd for $[C_{20}H_{25}O_4P+Na]$+requires m/z 383.1388. Found 383.1395 (ESI+).

Example 2
PBPC Peptide Synthesis

Peptides were synthesized on solid support using commercially available Wang polystyrene resin preloaded with the appropriate amino acid. Couplings were performed using 4 equiv amino acid derivative, 4 equiv. HBTU, and 3 equiv Hunig's base in DMF, for 3 h. Deprotections were performed using 20% piperidine in DMF for 20 mm (to minimize diketopiperazine formation, dipeptides were deprotected using 50% piperidine in DMF for 5 min). Peptides were cleaved from solid support using a mixture of MeOH:DMF:NEt$_3$ (9:1:1) for 4 d. The peptides were characterized by electrospray mass spectrometry and used in parallel reaction screens without further purification. Peptide 6 which proved selective for the desymmeterization of triol (3) was purified by reverse phase HPLC techniques. Preparative HPLC was performed using a reverse phase RP-18 X Terra (Waters) column, eluting with 57–73% methanol in water, at a flow rate of 4.15 mL/min. The purity was checked by analytical HPLC under similar conditions.

Data for Peptide 6
$^1$H NMR ($CDCl_3$, 400 MHz) δ 7.92 (s, 1H), 7.60 (d, J=7.0 Hz, 1H), 7.49 (d, J=8.1 Hz, 1H), 7.33–7.09 (m, 24H), 6.75 (s, 1H), 6.66 (s, 1H), 5.25 (d, J=–8.1 Hz, 1H), 4.94 (m, 2H), 4.69 (m, 1H), 4.51 m, 3H), 4.32 (m, 1H), 3.68 (s, 3H), 3.51 (s, 3H), 3.15–2.81 (m, 6H), 2.44 (d, J=4.8 Hz, 2H), 1.42 (s, 9H), 1.35 (s, 9H), 1.31 (d, J=7.3 Hz, 3H);
Low resolution mass calcd. for $[C_{60}H_{72}N_{10}O_{11}+H]$+requires m/z 1109.3. Found 1109.5 (ESI+);
Exact Mass calcd for $[C_{60}H_{72}N_{10}O_{11}-C_{19}H_{15}(trityl)+2H]$+ requires m/z 867.4365. Found 867.4358 (ESI±);
HPLC retention time 36.2 mm on a RP-18 X Terra (Waters) column eluting with a gradient of 57–73 % methanol/water over 40 mm, at a flow rate of 0.2 mL/min.

TABLE 1A

Data for Peptide Libraries

| Peptide | Sequence | Calcd M + H | Obs. M + H | ee % of 4 |
|---|---|---|---|---|
| A1 | BOC-Pmh-D-Pro-Aib-Phe-OMe | 613.34 | 613.33 | −5 |
| A2 | BOC-Pmh-D-Pro-Pro-Phe-OMe | 625.74 | 625.87 | 7 |
| A3 | BOC-Pmh-D-Val-D-Val-D-Pro-GIy-Leu-Val-D-Val-OMe | 947.59 | 947.59 | 14 |
| A4 | Boc-Pmh-D-Pro-Hfe-Phe-D-Phe-OMe | 836.99 | 836.22 | 16 |
| A5 | BOC-Pmh-D-Pro-D-Pip-Aib-Phe-OMe | 627.74 | 627.87 | 10 |
| A6 | BOC-Pmh-D-Pro-Phe-Hfe-D-Phe-OMe | 836.99 | 836.30 | 18 |
| A7 | BOC-Pmh-D-Pro-Hfe-Cha-D-Phe-OMe | 843.03 | 842.39 | 12 |
| A8 | BOG-Pmh-D-Pro-Cha-Phe-D-Phe-OMe | 829.01 | 828.37 | 14 |
| A9 | BOC-Pmh-D-Pro-Hfe-Phe-D-Phe-Phe-OMe | 984.16 | 938.42 | 11 |
| A10 | BOC-Pmh-DPro-2-amino-2-indan-2-carboxylic acid-Hfe-Phe-OMe | 849.00 | 848.25 | 10 |

TABLE 1A-continued

Data for Peptide Libraries

| Peptide | Sequence | Calcd M + H | Obs. M + H | ee % of 4 |
|---|---|---|---|---|
| A11 | BOC-Pmh-D-Pro-1-amino-1-cyclooctane carboxylic acid-Phe-OMe | 681.84 | 681.27 | 9 |
| A12 | BOC-Pmh-D-Pip-1-amino-1-cyclopentane carboxylic acid-Hfe-Phe-OMe | 814.98 | 814.53 | 12 |
| A13 | BOC-Pmh-D-Pip-Hfe-Phe-Phe-OMe | 851.01 | 850.23 | 7 |
| A14 | BOC-Pmh-D-Pip-Aib-Cha-Phe-OMe | 780.97 | 780.33 | 13 |
| A15 | BOC-Pmh-D-Pro-1-amino-1-cyclooctane carboxylic acid-Phe-OMe | 681.84 | 681.27 | −3 |
| A16 | BOC-Pmh-D-Pro-1-amino-1-cyclohexane carboxylic acid-Leu-Phe-OMe | 766.38 | 766.38 | 17 |
| A17 | BOC-Pmh-D-Pro-1-amino-1-cyclohexane carboxylic acid-Phe-OMe | 766.38 | 766.38 | 3 |
| A18 | BOC-Pmh-D-Pro-Hfe-D-Phe-Phe-OMe | 836.99 | 836.27 | −26 |
| A19 | BOC-Pmh-D-Pip-Hfe-D-Phe-OMe | 703.84 | 703.24 | 16 |
| A20 | BOC-Pmh-D-Pip-1-amino-1-cyclooctane carboxylic acid-Phe-OMe | 695.87 | 695.32 | 12 |
| A21 | BOC-Pmh-D-Pro-2-amino-2-indan carboxylicacid-Phe-Phe-OMe | 834.98 | 834.26 | 3 |
| A22 | BOC-Pmh-D-Pfo-1-amino-1-cyclooctane carboxylic acid-Chg-Phe-OMe | 821.04 | 820.38 | 4 |
| A23 | BOC-Pmh-D-Pro-2-amino-2-indan carboxylic acid-Phe-OMe | 687.81 | 687.23 | 1 |
| A24 | BOC-Pmh-D-Pro-1-amino-1-cyclohexane carboxylic acid-Cha-Phe-OMe | 807.01 | 806.37 | 7 |
| A25 | BOC-Pmh-Thr(But)-D-Glu(OBut)-Hfe-Ala-OMe | 859.04 | 859.14 | −9 |
| A26 | BOC-Pmh-D-Pro-Gly-1-amino-1-cyclohexane-Phe-OMe | 710.83 | 710.25 | −10 |
| A27 | BOC-Pmh-D-Val-Aib-D-Ala-Ala-OMe | 610.73 | 611.08 | −25 |
| A28 | BOC-Pmh-D-Glu(OBut)-Aib-Cha-Ala-OMe | 778.96 | 779.12 | 5 |
| A29 | BOC-Pmh-Asn(Trt)-His(πBn)-Asp-OBut-Ala-OMe | 1110.28 | 1110.11 | 90 |
| A30 | BOC-Pmh-Aib-Chg-Phe-Ala-OMe | 726.88 | 727.14 | 41 |
| A31 | BOC-Pmh-D-Pip-1-amino-1-cyclohexane carboxylic acid-Hfe-Phe-OMe | 829.02 | 828.28 | 16 |
| A32 | Boc-Pmh-Thr(OBut)-D-Val-His(Trt)-D-Phe-D-Val-Thr(OBut)-Ile-OMe | 1436 | 1436 | −25 |
| A33 | BOC-Pmh-His(πBn)-D-Glu(OBut)-Aib-Ala-OMe | 853.00 | 853.17 | −10 |
| A34 | BOC-Pmh-Leu-Ile-Phe-Ala-OMe | 728.89 | 729.15 | 8 |
| A35 | BOC-Pmh-D-Val-D-Glu(OBut)-Asp-OBut-Ala-OMe | 810.95 | 811.12 | 25 |
| A36 | BOC-Pmh-Phe-D-Glu(OBut)-Asn(Trt)-Ala-OMe | 1044.21 | 1044.15 | −14 |
| A37 | BOC-Pmh-Asn(Trt)-D-Ala-D-Glu(OBut)-Ala-OMe | 968.12 | 968.12 | −2 |
| A38 | BOC-Pmh-Asp-OBut-Leu-D-Glu(OBut)-Ala-OMe | 824.97 | 825.17 | −16 |
| A39 | BOC-Pmh-Ile-Cha-Aib-Ala-OMe | 706.89 | 707.16 | 29 |

Example 3
Phosphorylation of Triol 3.
Standard Conditions for Phosphorylation Employing DMAP Triol (3) (0.025 g, 0.057 mmol) was dissolved in 1.5 mL of CH$_2$Cl$_2$ and an aliquot of a DMAP solution in CH$_2$Cl$_2$ (50 μL, 0.0028 mmol, 5.0 mol %) was added. Triethylamine (9.0 ∥L, 0.065 mmol) was then introduced followed by diphenyl chlorophosphate (0.012 mL, 0.058 mmol). After 12 h the reaction was quenched with 0.5 mL of methanol and concentrated under reduced pressure. The starting material, the 1- and 5-mono phosphate products and the 1,3- and 1,5-diphosphate products were separated by preparative HPLC employing a normal phase YMC-Pack PVA-Sil NP column, eluting with a gradient of 0–6.5% 2-propanol/hexanes over 40 min, at a flow rate of 10 mL/min (see diagram 1 for HPLC trace). The five compounds were identified and characterized by $^1$H NMR, $^{31}$P NMR and Mass Spectrometry.

Example 4
Standard Conditions for Phosphorylation Using PBPC's

Parallel screening of the peptide catalysts in Table 1a were performed using either 25 mg or 50 mg of triol (3), as exemplified by the following experimental procedure. Triol 3 (0.050 g, 0.1 mmol) was dissolved in 2.5 mL of toluene. Each catalyst to be screened was dissolved in CH$_2$Cl$_2$ and an aliquot (50 μL, 0.0027 mmol, 2.5 mol %) was added to the reaction vessel. Triethylamine ( 0.021 mL, 0.15 mmol) was then added followed by diphenyl chlorophosphate (0.030 mL, 0.14 mmol). After 4 h the reactions were filtered to remove triethylamine salts, quenched with 1 mL of methanol and concentrated under reduced pressure. The crude reaction mixture was purified by preparative HPLC as reported above. The myo-inositol 1-phosphate peak was collected and the enantiomers were separated by chiral HPLC.

Example 5
Enantioselective Phosphorylation Using PBPC 6 and Product Isolation

Triol 3 (0.501 g, 1.11 mmol) was dissolved in 28 mL of toluene and an aliquot of peptide 6 in CH$_2$Cl$_2$ (0.50 mL, 0.028 mmol, 2.5 mol %) was delivered. The reaction was then cooled to 0° C. and triethylamine (0.170 mL, 1.22 mmol) was added followed by diphenyl chlorophosphate (0.230 mL, 1.11 mmol) which had been cooled to 0° C. After 2 h and 4 h additional triethylamine (0.085 mL, 0.61 mmol) and diphenyl chlorophosphate (0.115 mL, 0.55 mmol) were added. After 6 h the reaction was filtered to remove triethylamine salts, quenched with 4 mL of methanol, and concentrated under reduced pressure. Diol X was purified using silica gel flash chromatography eluting with 25% ethyl ether/toluene to yield 0.438 g (58% yield) of (4), which upon trituration with hexanes became a white solid.

(−)-2,4,6-Tri-O-benzyl-myo-inositol 1-phosphate (4)
$^1$H NMR (CDCl$_3$, 400 MHz) δ 7.38–7.14 (m, 25H), 4.91–4.63 (m, 6H), 4.59 (m, 1H), 4.25 (t, J=2.6 Hz, 1H), 3.95 (t, J=9.5 Hz, 1H), 3.72–3.55 (m, 3H), 2.42 (d, J=1.2 Hz, 1H), 2.21 (d, J=2.6 Hz, 1H);
$^{13}$C NMR (CDCl$_3$, 100 MHz) δ 150.3, 150.2, 138.3 (d, J=7.6 Hz), 138.0, 129.6 (d, J=6.9 Hz), 128.4, 128.3, 128.2, 127.9, 127.8, 127.8, 127.6 (d, J=10.7 Hz), 127.3, 125.3 (d, J=14.5 Hz), 120.0 (d, 3=4.6 Hz), 119.8 (d, J=5.3), 80.9, 80.1 (d, J=6.1 Hz), 79.8 (d, J=6.9 Hz), 78.9, 75.4, 75.2, 75.0, 74.7, 71.8;
$^{31}$P NMR (CDCl$_3$, 162 MHz) δ−11.7;
IR (film, cm$^{-1}$) 3402, 2099, 1646, 1485, 1282;
TLC R$_f$ 0.33 (50% ethyl ether/toluene);
$[α]_D$=−3.2 (1.0, CH$_2$Cl$_2$, at 99% ee);
Anal. Calcd. For C$_{39}$H$_{39}$O$_9$P: C, 68.61; H, 5.76; P, 4.54. Found: C, 68.56; H, 5.51; P, 4.36;
Exact mass calcd for [C$_{39}$H$_{39}$O$_9$P+Na]+requires m/z 705.2229. Found 705.2253 (ESI+);
HPLC retention time. 29.6 min employing a normal phase YMC-Pack PVA-Sil NP column, eluting with a gradient of hexanes to 6.5% 2-propanol/hexanes over 40 min, at a flow rate of 10 mL/min;
Assay of enantiomeric purity. Enantiomers of 4 were separated utilizing a Chiracel OD column (Alltech), eluting with 30% ethanol/hexanes at a flow rate of 0.5 mL/min. Retention times: myo-Inositol 1-phosphate: R$_{t(L)}$=11.5 min; R$_{t(D)}$=12.7 min.

2,4,6-Tri-O-benzyl-myo-inositol
$^1$H NMR (CDCl$_3$, 400 MHz) δ 7.41–7.30 (m, 15H), 4.85 (m, 6H), 4.02 (t, J=2.7 Hz, 1H), 3.61 (m, 5H);
Low resolution mass calcd for [C$_{27}$H$_{30}$O$_6$+Na]+requires m/z 473.2. Found 473.3 (ESI+);
HPLC Retention time. 28.5 min employing a normal phase YMC-Pack PVA-Sil NP column, eluting with a gradient of hexanes to 6.5% 2-propanol/hexanes over 40 min, at a flow rate of 10 mL/min.

2,4,6-Tri-O-benzyl-myo-inositol 1,5-diphosphate
$^1$H NMR (CDCl$_3$, 400 MHz) δ 7.40–6.98 (m, 35H), 4.86–460 (m, 8H), 4.31 (t, 3=2.6 Hz, 1H), 4.20 (t, J=9.5 Hz, 1H), 3.95 (t, J=9.5 Hz, 1H), 3.65 (m, 1H), 2.06 (d, J=5.1 Hz);
$^{31}$P NMR (CDCl$_3$, 162 MHz) δ−11.9, −11.9;
Low resolution mass calcd for [C$_{51}$H$_{48}$O$_{12}$P$_2$+Na]+requires m/z 937.2. Found 936.7 (ESI+)
HPLC Retention time. 33.9 min employing a normal phase YMC-Pack PVA-Sil NP column, eluting with a gradient of hexanes to 6.5% 2-propanol/hexanes over 40 min, at a flow rate of 10 mL/min.

2,4,6-Tri-O-benzyl-myo-inositol 1,3-diphosphate
$^1$H NMR (CDCl$_3$, 400 MHz) δ 7.37–7.09 (m, 35H), 4.76 (d, J=11.4 Hz, 2H), 4.68 (d, J=11.4 Hz, 2H), 4.62 (m, 2H), 4.50 (s, 2H), 4.49 (t, J=2.4 Hz, 1H), 3.97 (t, J=9.5 Hz, 2H), 3.62 (t, J=9.2, Hz, 1H);
$^{31}$P NMR (CDCl$_3$, 162 MHz) δ−12.0;
Low resolution mass calcd for [C$_{51}$H$_{48}$O$_{12}$P$_2$+Na]+requires m/z 937.2. Found 936.7 (ESI+);
HPLC Retention time. 34.8 min employing a normal phase YMC-Pack PVA-Sil NP column, eluting with a gradient of hexanes to 6.5% 2-propanol/hexanes over 40 min, at a flow rate of 10 mL/min.

2,4,6-Tri-O-benzyl-myo-inositol 5-phosphate
$^1$H NMR (CDCl$_3$, 400 MHz) δ 7.42–7.07 (m, 25H), 4.87–4.64 (m, 7H), 3.99 (t, J=2.9 Hz, 1H), 3.90 (t, J=9.5 Hz, 2H), 3.62 (dd, J=2.6 Hz, 9.5 Hz, 2H);
$^{31}$P NMR(CDCl$_3$, 162 MHz) δ−11.7;
Low resolution mass calcd for [C$_{39}$H$_{39}$O$_9$P+Na]+requires m/z 705.2. Found 705.0 (ESI+);
HPLC Retention time. 36.2 min employing a normal phase YMC-Pack PVA-Sil NP column, eluting with a gradient of hexanes to 6.5% 2-propanol/hexanes over 40 min, at a flow rate of 10 mL/min.

Example 6
(D)-myo-Inositol 1-phosphate Biscyclohexylamine Salt

Cleavage of both the phenyl and benzyl groups was achieved by a modification of a known procedure (Billington et al., *J. Chem. Soc. Perkins Trans. I*, (1989), 1423). Ammonia (20 mL) was condensed into 10 mL of THF at −77° C. under an atmosphere of argon. Lithium wire 0.5 cm was introduced into the solution, causing it to turn deep blue. A solution of diol 4 (0.90 g, 1.3 mmol) in THF (4 mL) was then added drop-wise until the solution became clear. Another piece of lithium wire (0.5 cm) was added and this titration procedure was continued until all the substrate was added. Lithium wire (0.5 cm) was then added and the reaction was stirred for 20 min, upon which time it was quenched with small pieces of ice. The solution was slowly warmed to room temperature and the ammonia was evaporated under a stream of argon. The resulting solids were taken up in 4 mL of H$_2$O and passed through a column of Dowex 500WX2-200 ion-exchange resin eluting with H$_2$O. The acidic fractions were collected and stirred with 3 mL of cyclohexylamine for 1 hr. The H$_2$O was removed by lyophilization to yield 0.58 g (96% yield) of myo-Inositol 1-phosphate biscyclohexylamine salt, which was recrystallized from acetone/water.

$^1$H NMR (D$_2$O, 400 MHz) δ 4.06 (t, J=2.7 Hz, 1H), 3.73 (m, 1H), 3.58 (t, J=9.5 Hz, 1H), 3.44 (m, 2H), 3.17 (t, J=9.2 Hz, 1H), 2.98 (m, 2H), 1.83–0.98 (m, 20H);
$^3$P NMR (D$_2$O, 162 MHz) δ 4.37;
$[α]_D$=3.5 (1.0, H$_2$O, at pH 9).

What is claimed is:

1. A stereoselective phosphorylation process for preparation of a cyclitol-monophosphate comprising the steps of:
    a) protecting at least one hydroxyl group in the cyclitol with a protecting group to provide a partially protected cyclitol
    b) reacting said partially protected cyclitol with a phosphorylating agent in the presence of a stereoselective phosphorylating catalyst of the formula

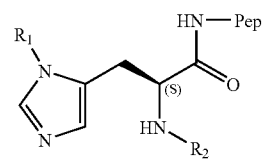

wherein R$_1$ is lower alkyl; R$_2$ is an amine protecting group; and Pep is a peptide comprising a peptide residue comprising at least one natural or non-natural amino acid; and
    c) deprotecting the partially protected cyclitol.

2. The phosphorylating catalyst of claim 1 wherein R$_1$=C$_1$ to C$_6$ straight or branched chain alkyl, R$_2$ is a carbamate group, and Pep is a monopeptide, an oligopeptide or a polypeptide comprising at least one amino acid.

3. The stereoselective phosphorylation process of claim 1 wherein the wherein the carbamate is selected from the group consisting of t-butyl carbamate, 9-fluorenylmethyl carbamate, benzyl carbamate and ortho-nitrobenzyl carbamate.

4. The stereoselective phosphorylation process of claim 1 wherein the carbamate is t-butyl carbamate.

5. The phosphorylating catalyst of claim 1 wherein $R_1$ is $CH_3$, $R_2$ is t-butylcarbamate, and Pep is a an oligopeptide or a polypeptide comprising a sequence of 2 to 50 amino acids.

6. The phosphorylating catalyst of claim 1 wherein $R_1$ is $CH_3$, $R_2$ is t-butylcarbamate, and Pep is a an oligopeptide or a polypeptide comprising a sequence of 2 to 8 amino acids.

7. The stereoselective phosphorylation process of claim 1 wherein the phosphorylation catalyst is:

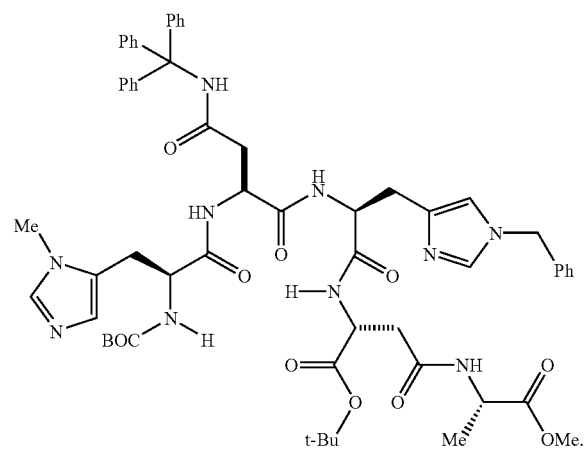

8. A stereoselective phosphorylation process for the preparation of a cyclitol-monophosphate comprising the steps of:
   a) protecting at least one hydroxyl group in the cyclitol with a protecting group to provide a partially protected cyclitol;
   b) reacting said partially protected cyclitol with a phosphorylating agent in the presence of a stereoselective phosphorylating catalyst of the formula; and
   c) deprotecting the partially protected cyclitol,
wherein the phosphorylation catalyst is:

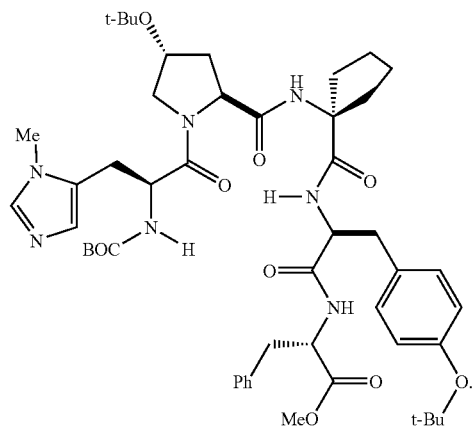

9. The stereoselective phosphorylation process of claim 1 wherein the phosphorylation agent is a dichlorodiakyl phosphate, dichlorodiarylphosphate, or derivatives thereof.

10. The stereoselective phosphorylation process of claim 1 wherein the phosphorylation agent is dichlorodiphenyl phosphate.

11. The stereoselective phosphorylation process of claim 1 wherein the cyclitol is an inositol.

12. The stereoselective phosphorylation process of claim 11 wherein the inositol is myo-inositol.

13. The stereoselective phosphorylation process of claim 1 wherein the cyclitol monophosphate is myo-inositol monophosphate.

14. The stereoselective phosphorylation process of claim 13 wherein the inositol monophosphate (D)-myo-inositol-1-phosphate.

15. The stereoselective phosphorylation process of claim 13 wherein the inositol monophosphate (D)-myo-inositol-3-phosphate.

16. A compound of the formula

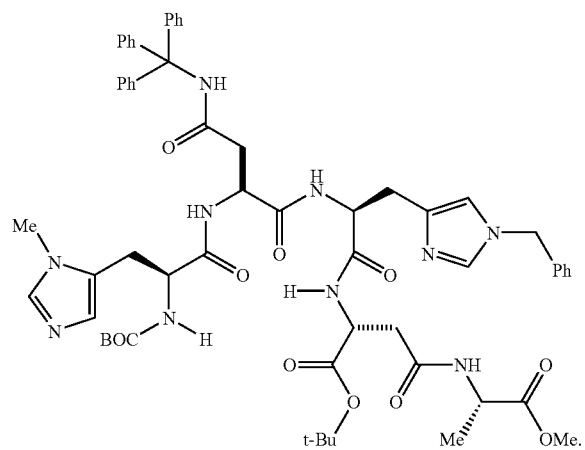

17. A compound of the formula

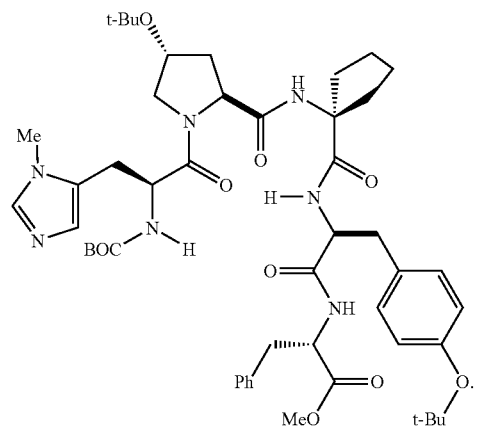

* * * * *